United States Patent
Schroeder

(10) Patent No.: US 6,341,472 B1
(45) Date of Patent: Jan. 29, 2002

(54) METHOD AND FACILITY FOR SEALING BOTTLES WITH STERILE SEALING CAPS

(75) Inventor: Klaus Schroeder, Ahaus (DE)

(73) Assignee: GEA Finnah GmbH, Ahaus (DE)

( * ) Notice: Subject to any disclaimer, the term of this patent is extended or adjusted under 35 U.S.C. 154(b) by 0 days.

(21) Appl. No.: 09/402,152

(22) PCT Filed: Jun. 27, 1998

(86) PCT No.: PCT/EP98/03940

§ 371 Date: Oct. 19, 1999

§ 102(e) Date: Oct. 19, 1999

(87) PCT Pub. No.: WO99/01374

PCT Pub. Date: Jan. 14, 1999

(30) Foreign Application Priority Data

Jul. 1, 1997 (DE) .......................... 197 27 942

(51) Int. Cl.⁷ .................... B65B 55/04; B65B 7/28
(52) U.S. Cl. ...................... 53/426; 53/306; 53/317; 53/331.5; 53/485; 53/488
(58) Field of Search .................. 53/167, 306, 307, 53/308, 317, 331.5, 426, 488, 485

(56) References Cited

U.S. PATENT DOCUMENTS

| 3,626,658 A | * | 12/1971 | Jones | 53/307 |
| 3,861,118 A | * | 1/1975 | Muto | 53/167 |
| 4,040,236 A | * | 8/1977 | Siler, Jr. et al. | 53/317 |
| 4,205,502 A | * | 6/1980 | Ahlers | 53/331 |
| 5,054,260 A | * | 10/1991 | Herzog | 53/307 |
| 5,129,212 A | * | 7/1992 | Duffey et al. | 53/426 |
| 5,660,100 A | * | 8/1997 | Spelten et al. | 99/356 |
| 5,848,515 A | * | 12/1998 | Catelli et al. | 53/167 |

* cited by examiner

Primary Examiner—Peter Vo
Assistant Examiner—Nathaniel Chuckwurah
(74) Attorney, Agent, or Firm—Jordan and Hamburg LLP

(57) ABSTRACT

A machine for sealing bottles with sealing caps includes a transporting track for supplying sealing caps, a separating device for making available separated sealing caps and a transfer device for placing the separated sealing caps on the bottles. At least the transfer device is disposed in a sterile chamber and a spraying device is provided for introducing a sterilizing agent into the interior space of the sealing caps and a drying device is also provided for driving sterilizing agent out of the sealing caps.

9 Claims, 3 Drawing Sheets

METHOD AND FACILITY FOR SEALING BOTTLES WITH STERILE SEALING CAPS

Figure 1:
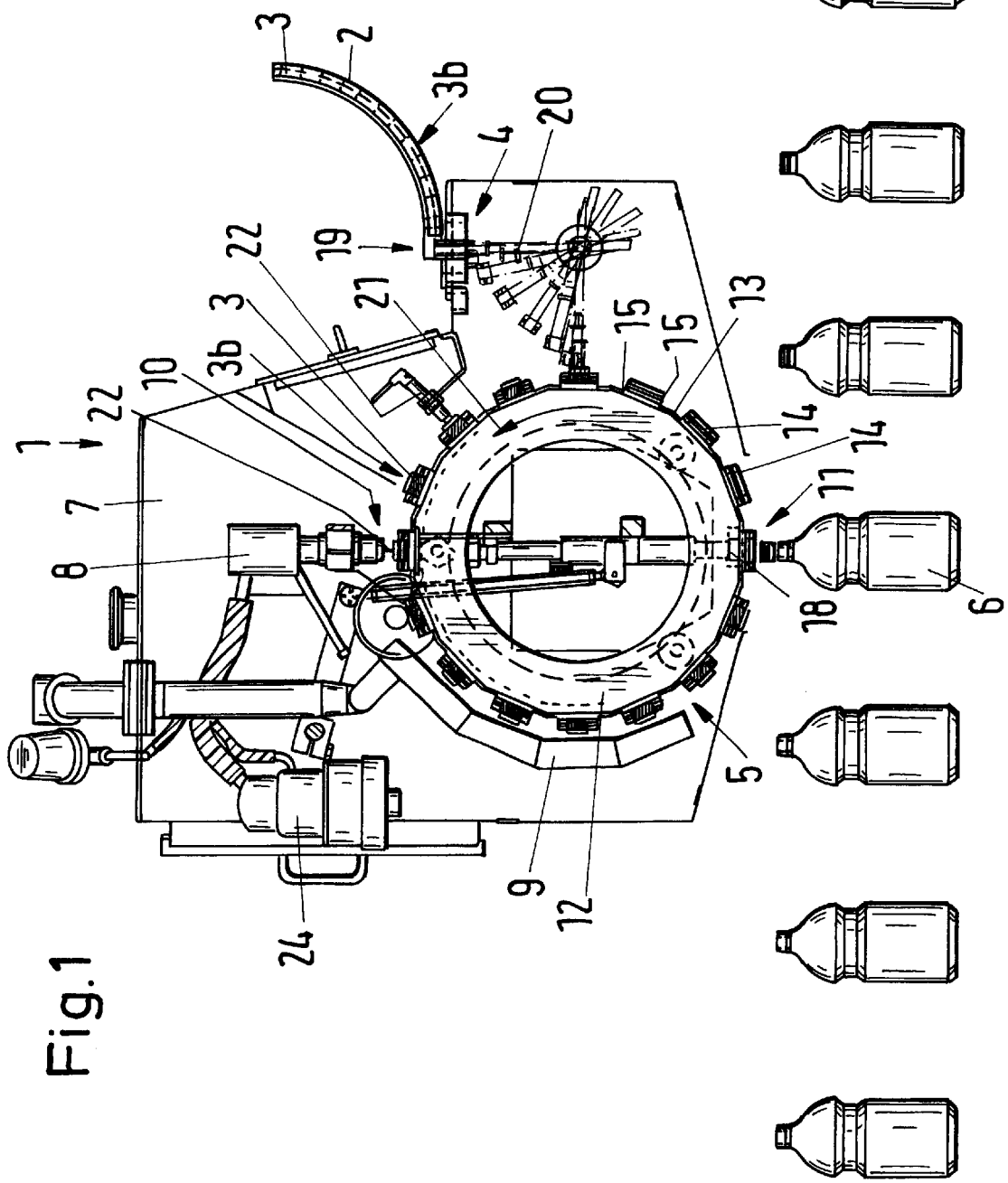

The invention relates to a machine for sealing bottles with sealing caps. Machines of this type find use for plastic as well as for glass bottles in bottle filling installations, screw caps, crown corks or other seals being used as sealing caps.

SUMMARY OF THE INVENTION

The inventive method and machine ensure that a sterilization of the sealing caps is carried out, before the caps are placed on the bottles, the sterility being maintained until the sealing cap is put in place owing to the fact that the transfer device is disposed completely in a sterile chamber. The drying equipment in the sterile chamber avoids a contamination of the openings of the bottles by residues of sterilizing agents. Moreover, an operation with short cycling times is possible, as is required in high-performance filling plants.

Further details and effects arise out of the following description of an example of the object of the invention, shown in the accompanying drawings

IN THE DRAWINGS

Figure 2:
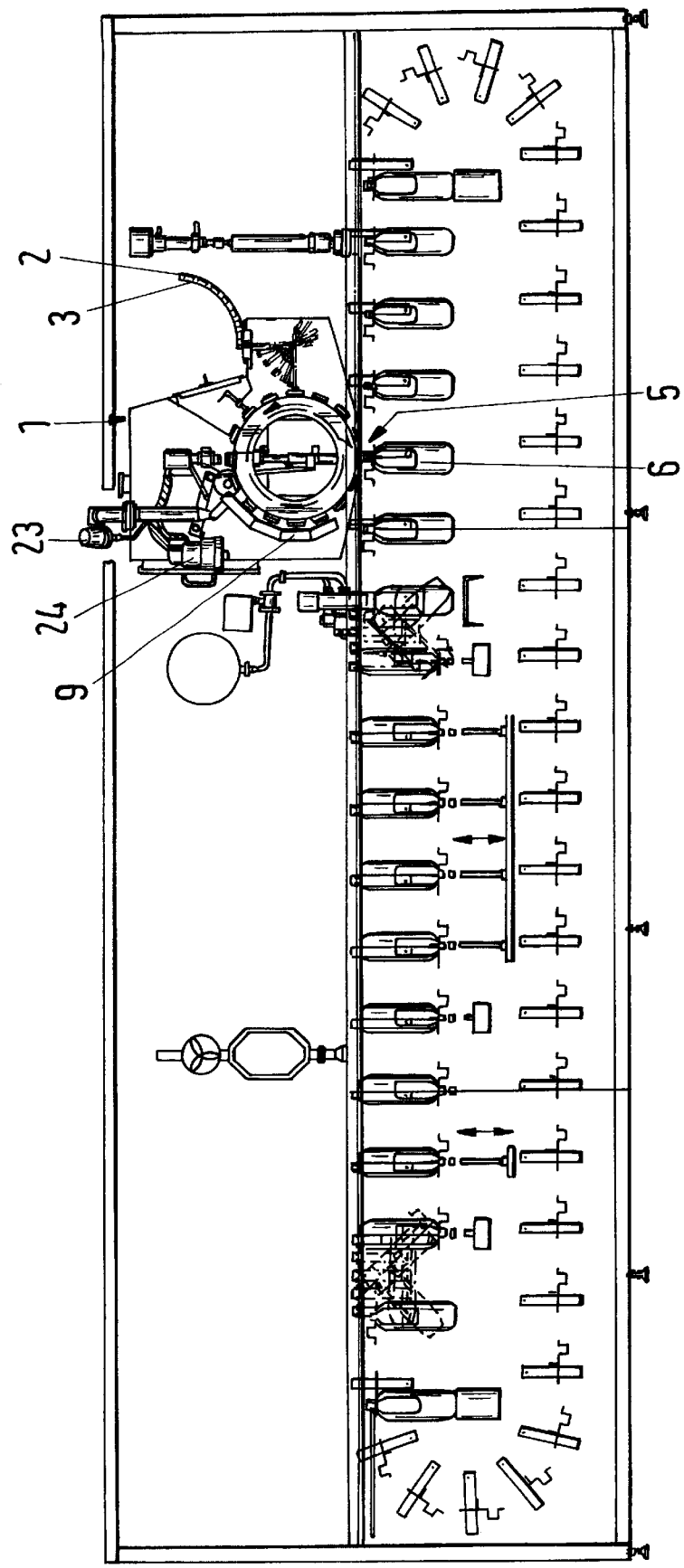
Figure 3:
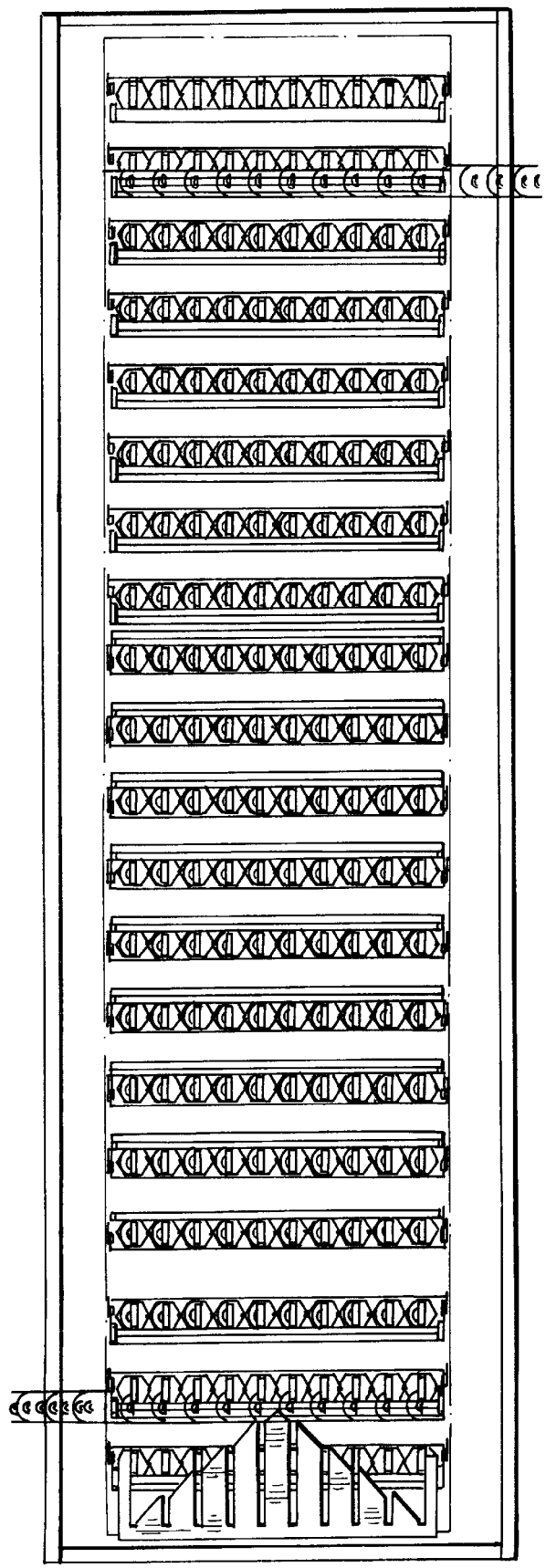

FIG. 1 shows an inventive machine in a partially sectional, side view,

FIG. 2 in a side view, shows the arrangement of the machine of FIG. 1 in an installation for filling bottles under sterile conditions, and FIG. 3 shows a diagrammatic plan view of the bottle conveyor of the installation of FIG. 2.

DESCRIPTION OF THE PREFERRED EMBODIMENTS

As can be seen from FIG. 1, the machine 1 has a transporting track 2, which is charged from a storage tank, which is not shown. Adjoining the transporting track 2, there is a separating device 4, which makes available the sealing caps 3 in individual positions. The machine furthermore comprises a transfer apparatus 5, by means of which the separated sealing caps 3 are placed on bottles 6, which are transported along a bottle transporting track below the machine 1.

In a sterile chamber 7, a separating device 4 for the sealing caps 3, which is assigned to the transporting track 2 at its end and in which, in the example shown, there is also a downstream transfer device 5, is disposed. The sealing caps 3, which go over to the transfer device 5, are therefore no longer exposed to the outside air and instead, after leaving the transporting track 2, are in a sterile environment. Spraying equipment 8, assigned to the upper side of the transfer device in the upper culmination point of this device, acts upon the sealing caps 3 located in the transfer device 5 with a sterilizing agent, which is sprayed into the interior space 3b of the sealing caps 3. For this purpose, the sealing caps 3, while the sterilizing agent is being sprayed in, are in a position, in which their interior points upward. Therefore, before they are transferred to the bottle openings, the sealing caps 3 must be turned, so that the interior space 3b faces downward and the sealing caps can be placed on the bottles 6.

Furthermore, drying equipment 9, which is effective in a region between the place, where the sealing caps are acted upon with the sterilizing agent and the place, where the sealing caps are transferred to the bottles 6, is assigned to the transfer device 5. The drying equipment 9 acts on the sealing caps 3 and especially on their interior spaces 3b with sterilized hot air at about 70° C., which blows residues of sterilizing agents out of the sealing caps 3 while the latter are being turned from the sterilization position 10 into a position 11, in which they can be placed on the bottles 6.

In the example, the transfer device 5 is at the same time designed for turning the sealing caps 3 from the sterilization position 10 into the setting-down position 11 and constructed as a star wheel 12, which revolves in a vertical plane and is provided over its periphery 13 with accommodating elements 14 for the sealing caps 3, which are distributed at regular intervals over the outer periphery 13 of the star wheel 12. These accommodating elements 14 are constructed as clamping elements, which hold the sealing caps 3 and grip around the latter in their upper region, which is averted from the opening of the interior space 3b. However, the clamping elements can also grip around the entire side walls of the sealing caps 3. The clamping action can be brought about by clamping jaws 15, which are provided with, for example, elastomeric elements, which accommodate the sealing caps 3, holding them. The sealing caps 3 can be moved out of this holding position in the accommodating elements 14 by means of a punch 16, which is movable along a vertical axis 17 and acts on the sealing caps 3, located in the setting-down position 11 in such a manner, that the punch 16 presses the sealing caps 3 out of the accommodating elements 14 and places them onto the bottle 6 below.

In order to prevent free fall during this setting-down motion, the punch 16 includes at its front region 18 a suction or gripping device, which connects the respective sealing cap 3 detachably with the punch 16, before the sealing cap 3 is ejected from the accommodation elements 14.

For placing a sealing cap 3 on the bottle 6, an additional, downwards directed pressure is exerted by the punch 16 on the sealing cap 3, so that the sealing cap 3 already receives a certain security on the mouth of the bottle. This is desirable especially in the case of screw caps, so that these already grip the thread with their retaining ring and are finally fixed by a rotating device, which is downstream from the machine 1.

Alternatively, the punch 16 can also, at least with its front part 18, be rotatable about the vertical axis 17, in order to make screwing of the sealing cap possible already during the setting-down process. For crown cork-like sealing caps, a compression unit, which lies around the sides of the crown cork about an opening bulge of the bottle, can be disposed at the front region 18 of the punch 16.

For supplying the sealing caps 3 to the sterile chamber 7, the example shown provides, as transporting track, a chute 2, which discharges at the inlet opening 19 into the sterile chamber and guides the sealing caps 3 in single file in contact with one another and makes them available with the interior space 3b pointing downward at the inlet opening 19. At the inlet opening 19, the sealing caps 3 are taken over by the separating device 4, which accepts the sealing caps 3, for example, by means of a punch 20, such as a suction punch. In the example, the punch 20 is constructed so that, aside from a vertical lifting motion, which enables it to reach through the inlet opening 19, it can carry out a superimposed swiveling motion about a horizontal axis and, after swiveling through an angle of about 90°, reach a horizontal position in which, in a horizontally traveling motion, the sealing caps 3 taken up are transferred to the star wheel 12 of the transfer device 5. During this traveling motion, the punch 20 forces the respective sealing cap 3 into an in-phase available, accommodating element 14 of the star wheel 12. For its linear and swiveling motions, the punch 20 includes its own suitable driving mechanisms, the details of which are not shown, such as an electromagnetic driving mechanism for the linear movement and a pressure medium driving mechanism for a swiveling drive unit.

The device for holding the sealing cap 3 on the punch 20 can be operated, for example, by means of a vacuum or by means of a mechanical gripper.

The punch 20 is synchronized with the timed rotation of the star wheel 12 in such a manner, that each accommodating element 14, on passing by the separating device 4, is equipped with a sealing cap 3.

The star wheel 12 transports the sealing caps 3, which have been taken up, in the direction of the arrow 21 initially past a detector unit 22, which checks, for example, by means of photodiodes, whether each passing accommodating element 14 is provided with a sealing cap 3.

In the further course of the movement, the sealing caps 3 are brought consecutively into the sterilizing position 10, in which their upwardly pointing interior space 3b is placed below the spraying device 8 and acted upon with a sterilizing agent.

The spraying device 8 can be constructed as an ultrasonic atomizer for atomizing the sterilizing agent, which is introduced over a front nozzle 22 into the interior spaces 3b of the caps.

For this purpose, the spraying device 8 is connected with a tank 23, holding the sterilizing agent, as well as with a tank 24, holding sterile air, in order to be able to bring a mixture of sterilized air and a sterilizing agent, such as hydrogen peroxide ($H_2O_2$) into the interior spaces 3b of the caps. Basically, such a spraying device 8 is known from the EP 0 272 538 B 1. Instead of hydrogen peroxide, it is also possible to use other sterilizing agents, such as hot steam, the use of which will depend on Food Law Regulations in force and the respective circumstances.

After the sealing caps 3 are sprayed with sterilizing agent, they are turned in the further course of the star wheel motion, the drying device 9 being effective over the essential part of the motion from the sterilizing position 10 into the setting-down position 11 and, in its region of action, acting upon the sealing caps 3 with sterilized air. By these means, it is ensured that residue of the sterilizing agent do not remain in the interior spaces 3b of the caps or possibly reach the mouth of the bottle.

Due to the action of the drying air, initially also the outside of the sealing caps 3 are wetted with sterilizing agent which, after being driven out of the interior space 3b by the air, is blown on the outside along the side walls. Because the drying device 9 extends along a considerable portion of the circular path of the transfer device 5, several sealing caps 3 can be acted upon with sterile air simultaneously.

The sterile chamber 7 is under an overpressure, so that surrounding air, which could cause contamination of the sealing caps 3, cannot penetrate from outside through the chambers, which are open at the bottom in the region of the setting-down position 11. Since the open bottles 6, which have already been filled, are also kept in an environment of sterile air up to the setting-down position 11, the bottle openings are also sterile, so that, overall, sterile filling is ensured. If the conveyor, transporting the bottles 6 to the machine 1 is also moving in a sterile space, the pressure in this sterile space appropriately is higher than the pressure in the sterile chamber 7 of the machine 1, in order to prevent residues of sterilizing agent being transferred to the bottles 6. In this case, a vacuum connection piece 24, leading to a pump, is provided in the upper region of the sterile chamber 7 for aspirating air out of the sterile chamber 7.

If, as is shown in FIGS. 2 and 3, the machine 1 works together with a multi-row filling installation, as described in detail in the German patent application 197 00 156.4-23, the machine 1 can consist of a corresponding parallel arrangement of similar components for supplying, preparing and putting in place sealing caps 3, in order to close off the bottles 6 simultaneously with sealing caps on several parallel, conveyor belts.

In all therefore, the intervention has made possible a method, for which the sealing caps are supplied over a transporting track, in which they are still freely accessible and can be subjected to a quality control in the sense of a sorting out of defective sealing caps, to a transfer device, which then takes over the sealing caps in separated positions. After the defective sealing caps have been sorted out, a high functional reliability of the transfer is assured. The sealing caps are supplied to the transfer device directly or indirectly with the interior space pointing downward, then turned by the transfer device so far, that the interior space points upward and can be sprayed with sterilizing agent. After a further turning, the sealing caps are dried, before they are placed on the bottles with the interior space pointing downward.

What is claimed is:

1. Apparatus for sealing containers with sealing caps in which the sealing caps have an interior space and an interior space opening comprising:
   a sterile chamber;
   a transfer device disposed in said sterile chamber for transporting said sealing caps and for placing said sealing caps on said containers;
   a sealing cap supply device for supplying sealing caps to said transfer device and including a transport device for transporting said sealing caps and a separation device for taking separate sealing caps from said transport device and transferring said separate sealing caps to said transfer device;
   a container supply device for supplying containers to said transfer device;
   a sterilizing device in said sterile chamber for introducing a sterilizing agent into the interior space of the sealing caps on said transfer device; and
   a drying device in said sterile chamber for removing said sterilizing agent from the interior space of said sealing caps.

2. Apparatus for sealing containers with sealing caps in which the sealing caps have an interior space and an interior space opening comprising:
   a sterile chamber having an opening;
   a transfer device disposed in said sterile chamber for transporting said sealing caps and for placing said sealing caps on said containers, said transfer device including:
     a rotatable body rotatable about a generally horizontal axis, said rotatable body having:
       an outer periphery and a plurality of spaced placement devices on the outer periphery of said rotatable body,
       each of said placement device accommodating a sealing cap;
   said transfer device being operable to sequentially position said placement devices adjacent to said opening;

a sealing cap supply device for supplying sealing caps to said transfer device;

a container supply device for supplying containers to said transfer device;

a sterilizing device in said sterile chamber for introducing a sterilizing agent into the interior space of the sealing caps on said transfer device; and a drying device in said sterile chamber for removing said sterilizing agent from the interior space of said sealing caps.

3. Apparatus for sealing containers according to claim 2 further comprising a sterile air device for introducing sterile air into said sterilizing chamber and for maintaining the pressure in said sterilizing chamber greater than atmospheric chamber.

4. Apparatus for sealing containers with sealing caps in which the sealing caps have an interior space and an interior space opening comprising:

a sterile chamber;

a transfer device disposed in said sterile chamber for transporting said sealing caps and for placing said sealing caps on said containers, said transfer device including:

a rotatable body rotatable about a generally horizontal axis, said rotatable body having:

an outer periphery and a plurality of spaced placement devices on the outer periphery of said rotatable body, each of said placement device accommodating a sealing cap and including a holder on said rotatable body which holds said sealing caps on said rotatable body and including elastomeric elements;

a sealing cap supply device for supplying sealing caps to said transfer device;

a container supply device for supplying containers to said transfer device;

a sterilizing device in said sterile chamber for introducing a sterilizing agent into the interior space of the sealing caps on said transfer device; and a drying device in said sterile chamber for removing said sterilizing agent from the interior space of said sealing caps.

5. Apparatus for sealing containers with sealing caps in which the sealing caps have an interior space and an interior space opening comprising:

a sterile chamber;

a transfer device disposed in said sterile chamber for transporting said sealing caps and for placing said sealing caps on said containers, said transfer device having:

a plurality of spaced placement devices on which sealing caps are disposed, a plurality of operating positions for changing the location of said placement devices, and one operating position in which a first placement device is located in one location, the sealing cap disposed on said first placement device in said one location having its interior space opening facing downwardly;

a sealing cap supply device for supplying sealing caps to said transfer device;

a container supply device for supplying containers to said transfer device;

a sterilizing device in said sterile chamber for introducing a sterilizing agent into the interior space of the sealing caps on said transfer device;

a drying device in said sterile chamber for removing said sterilizing agent from the interior space of said sealing caps;

said sterile chamber having a chamber opening juxtaposed to said one location;

said container supply device being operable to dispose a container in a receiving position juxtaposed to said chamber opening; and said transfer device having an operating mechanism for effecting transfer of said sealing cap from said one location to a position on said container when said container is in said receiving position, wherein said chamber opening underlies said operating mechanism when said placement device is in said one location, said chamber opening overlying said container when said container is in said receiving position.

6. Apparatus for sealing containers with sealing caps in which the sealing caps have an interior space and an interior space opening comprising:

a sterile chamber;

a transfer device disposed in said sterile chamber for transporting said sealing caps and for placing said sealing caps on said containers, said transfer device having:

a plurality of spaced placement devices on which sealing caps are disposed, a plurality of operating positions for changing the location of said placement devices, and one operating position in which a first placement device is located in one location, the sealing cap disposed on said first placement device in said one location having its interior space opening facing downwardly;

a sealing cap supply device for supplying sealing caps to said transfer device;

a container supply device for supplying containers to said transfer device;

a sterilizing device in said sterile chamber for introducing a sterilizing agent into the interior space of the sealing caps on said transfer device;

a drying device in said sterile chamber for removing said sterilizing agent from the interior space of said sealing caps;

said sterile chamber having a chamber opening juxtaposed to said one location;

said container supply device being operable to dispose a container in a receiving position juxtaposed to said chamber opening;

said transfer device having an operating mechanism for effecting transfer of said sealing cap from said one location to a position on said container when said container is in said receiving position;

said operating mechanism having a gripper unit for gripping the sealing cap as said sealing cap is transferred from said one location on said first placement device to said position on said container; and said gripper unit including a suction device.

7. Apparatus for sealing containers with sealing caps in which the sealing caps have an interior space and an interior space opening comprising:

a sterile chamber;

a transfer device disposed in said sterile chamber for transporting said sealing caps and for placing said sealing caps on said containers, said transfer device having:

a plurality of spaced placement devices on which sealing caps are disposed, a plurality of operating positions for changing the location of said placement devices, and one operating position in which a first placement device is located in one location, the sealing cap disposed on said first placement device in said one location having its interior space opening facing downwardly;

a sealing cap supply device for supplying sealing caps to said transfer device;

a container supply device for supplying containers to said transfer device;

a sterilizing device in said sterile chamber for introducing a sterilizing agent into the interior space of the sealing caps on said transfer device;

a drying device in said sterile chamber for removing said sterilizing agent from the interior space of said sealing caps;

said sterile chamber having a chamber opening juxtaposed to said one location;

said container supply device being operable to dispose a container in a receiving position juxtaposed to said chamber opening; and said transfer device having an operating mechanism for effecting transfer of said sealing cap from said one location to a position on said container when said container is in said receiving position, wherein said sterile chamber opening is designated a first chamber opening, said sterile chamber having a second chamber opening, said supply device having a supply track for said sealing caps leading to said second chamber opening such the sealing caps pass through said second chamber opening into said sterile chamber.

8. Apparatus for sealing containers according to claim 7 wherein the interior space opening of said sealing caps face downwardly as said sealing caps pass through said second chamber opening into said sterile chamber.

9. Apparatus for sealing containers according to claim 7 wherein said sealing cap supply device includes a passing-along device which takes a sealing cap from said supply track at said second chamber opening and transfers the last said sealing cap to one of said placement devices on said rotatable body.

* * * * *